United States Patent
Kramer et al.

(10) Patent No.: US 8,709,477 B2
(45) Date of Patent: Apr. 29, 2014

(54) PHARMACEUTICAL DOSAGE FORM

(75) Inventors: Dirk Kramer, Herznach (CH); Helene Rey, Rosenau (FR); Mathias Scheer, Wehr (DE)

(73) Assignee: Kremers Urban Pharmaceuticals, Inc`, Princeton, NJ (US)

( * ) Notice: Subject to any disclaimer, the term of this patent is extended or adjusted under 35 U.S.C. 154(b) by 0 days.

(21) Appl. No.: 13/390,090

(22) PCT Filed: Aug. 13, 2010

(86) PCT No.: PCT/US2010/045489
§ 371 (c)(1),
(2), (4) Date: Apr. 3, 2012

(87) PCT Pub. No.: WO2011/020032
PCT Pub. Date: Feb. 17, 2011

(65) Prior Publication Data
US 2012/0189695 A1    Jul. 26, 2012

Related U.S. Application Data

(60) Provisional application No. 61/233,809, filed on Aug. 13, 2009.

(51) Int. Cl.
*A61K 9/20* (2006.01)
*A61K 9/24* (2006.01)
*A61K 8/28* (2006.01)
*B01J 13/00* (2006.01)
*B05D 3/00* (2006.01)
*A61K 31/445* (2006.01)

(52) U.S. Cl.
USPC ........... 424/465; 424/472; 427/2.14; 514/317

(58) Field of Classification Search
None
See application file for complete search history.

(56) References Cited

U.S. PATENT DOCUMENTS

| 2,957,880 | A | | 10/1960 | Rometsch | |
|---|---|---|---|---|---|
| 6,136,345 | A | * | 10/2000 | Grimmett et al. | 424/471 |
| 6,419,960 | B1 | * | 7/2002 | Krishnamurthy et al. | 424/490 |
| 6,919,337 | B2 | | 7/2005 | Bahlay et al. | |
| 6,930,129 | B2 | | 8/2005 | Lam et al. | |
| 2003/0035839 | A1 | * | 2/2003 | Hirsh et al. | 424/471 |
| 2004/0197406 | A1 | * | 10/2004 | Prater et al. | 424/470 |

FOREIGN PATENT DOCUMENTS

WO    WO/97/03672    2/1997

OTHER PUBLICATIONS

Donbrow, M. and Samuelov, Y. Zero order drug delivery from double-layered porous films: release rate profiles from ethyl cellulose, hydroxylpropyl cellulose and polyethylene glycol mixtures. J. Pharm. Pharmacol. 1980, 32;463-470.*
Hypromellose Acetate Succinate. FDA Inactive Ingredient Database. <http://www.accessdata.fda.gov/scripts/cder/iig/index.cfm>. accessed Apr. 11, 2013.*
Hydroxypropyl Cellulose. FDA Inactive Ingredient Database. <http://www.accessdata.fda.gov/scripts/cder/iig/index.cfm>. accessed Apr. 17, 2013.*

* cited by examiner

*Primary Examiner* — Kortney L Klinkel
*Assistant Examiner* — Nicole Babson
(74) *Attorney, Agent, or Firm* — Ted Whitlock

(57) ABSTRACT

This invention relates to a oral pharmaceutical formulation for methylphenidate or its analogs, derivatives, isomers or enantiomers, including d-threo-methylphenidate.

14 Claims, No Drawings

PHARMACEUTICAL DOSAGE FORM

CROSS REFERENCE TO RELATED APPLICATIONS

This is a national stage filing under 35 USC §371 claiming the benefit of International PCT Application PCT/US2010/045489 filed Aug. 13, 2010, which claims priority to U.S. Provisional Application, Ser. No. 61/233,809, filed Aug. 13, 2009.

FIELD OF THE INVENTION

This invention relates to a composition comprising methylphenidate or its analogs, derivatives, isomers or enantiomers, including d-threo-methylphenidate.

BACKGROUND OF THE INVENTION

Methylphenidate is a chiral molecule. The properties of the enantiomers have been investigated to some extent, although the drug is still administered as the racemate. It is generally thought that d-threo-methylphenidate is the active metabolite.

Methylphenidate is a known drug and controlled substance used primarily to treat hyperactive children. Attention Deficit Disorder (ADD) and Attention Deficit/Hyperactivity Disorder (ADHD) (severally and collectively hereinafter referred to as "ADD") are developmental disorders of self-control. They consist of problems with attention span, impulse control and activity level. These problems are reflected in impairment of a person's will or capacity to control his or her own behavior relative to the passage of time and to keep future goals and consequences in mind.

Traditionally, methylphenidate has been used as a drug of choice for the treatment of ADD in both children and adults for several reasons. Methylphenidate, described in U.S. Pat. No. 2,957,880, is a central nervous system stimulant. Though not an amphetamine, methylphenidate functions in the brain in a way similar to amphetamines. Current commercially available dosage forms containing methylphenidate are marketed under the names Ritalin® and Concerta® tablets.

U.S. Pat. Nos. 6,919,337 and 6,930,129 to Alza Corporation teach a dosage form and a method of administering methylphenidate in a controlled release formulation providing an ascending release rate. The dosage form disclosed in the '337 and '129 patents comprises a layered tablet core including an expanding "push layer" which serves to facilitate release of the active ingredient contained within the tablet.

International patent application, PCT Publication No. WO 97/03672 (Chiroscience Ltd.), discloses that methylphenidate exhibits a therapeutic effect when administered in the form of a racemic mixture or in the form of a single isomer (such as the RR d-threo enantiomer). Further, WO 97/03763 (Chiroscience Ltd.) discloses a sustained release formulation containing the d-threo-methylphenidate (dtmp) enantiomer. This disclosure teaches the use of a composition comprising a coating through which the dtmp passes in order to attain sustained release and achieve serum levels (of the active ingredient) of at least 50% $C_{max}$ over a period of at least 8 hours.

There is an unmet commercial need for a formulation which can provide controlled or sustained release dosage form containing methylphenidate which can be manufactured using a conventional pharmaceutical manufacturing process that can be advantageous to consumers and insurers.

SUMMARY OF THE INVENTION

A formulation of the subject invention is preferably prepared in five (5) primary manufacturing steps: (1) preparation of Active Beads; (2) preparation and application of a Sustained Bead Coating; (3) preparation and application of a Controlled Release Bead Coating; (4) preparation of a Final Blend and Tablet Compression to form a Tablet Core which is coated using a portion of a prepared Seal Coat Solution; and (5) application of an Active Immediate-Release Coating, followed by a seal coating using the remainder of the prepared Seal Coat Solution and then a color coating, to arrive at the final product.

A resulting dosage form of the subject invention, as prepared by the above manufacturing steps, is preferably provided as a tablet, but can be further enclosed in a capsule or provided as a suspension.

A dosage form of the subject invention can be useful for the treatment of Attention Deficit Disorder (ADD) and Attention Deficit/Hyperactivity Disorder (ADHD) or other conditions known to respond to treatment using methylphenidate, its isomers, derivatives, analogs, or the like.

DETAILED DESCRIPTION OF THE INVENTION

A preferred embodiment of the subject formulation and dosage form comprises coated beads or pellets containing methylphenidate, or an analog, derivative, isomer or prodrug of methylphenidate (hereinafter, severally and collectively, the "active drug") forming an active, extended release tablet core, which can be further coated with an immediate-release coating, also containing active drug.

A preferred embodiment of the subject invention comprises a controlled release active pellet or bead comprising active drug and a pharmaceutically acceptable excipient, such as a cellulosic hydrogel, and may further include a filler or binder. The controlled release bead or pellet is then preferably coated using a sustained release coating, and further comprises a controlled release coating, e.g., an enteric coating, which is different than the sustained release coating. A preferred sustained release coating can comprise a rate controlling polymer, such as the cellulose-based hydrogel excipients, e.g., ethyl cellulose, hydroxypropyl cellulose, hydroxypropyl methylcellulose (HPMC), or the like, and can include a plasticizer, such as triethyl acetate, or the like.

The controlled release coating can preferably comprise an enteric coating component such as hypromellose acetate succinate. Other commonly-used and well-known enteric coatings, which resist dissolution in basic solutions (and typically do not dissolve in solutions having a pH below 5.5), include methacrylic acid copolymers, cellulose acetate and its succinate and phthalate forms, styrol maleic acid co-polymers, polymethacrylic acid/acrylic acid copolymer, hydroxypropyl methyl cellulose phthalate, polyvinyl polymers, including polyvinyl acetate phthalate, hydroxyethyl ethyl cellulose phthalate, hydroxypropyl methyl cellulose acetate succinate, cellulose acetate tetrahydrophtalate, acrylic resin, timellitate, shellac, and the like.

Following application of the sustained and controlled release coatings, the beads or pellets can be formed as a tablet core, preferably using a conventional single-layer tablet press to compress the coated beads or pellets, as is well known in the art. The compressed beads or pellets of the tablet core of the subject invention, although having one or more coatings layered thereon, are not considered as layered tablet cores because the coated beads or pellets form a non-homogenous single layer core.

Preferably, compression of the coated beads or pellets is carried out in the presence of a lubricant, e.g., hydroxypropyl methylcellulose (also having solubilizer properties), and can include a binder, such as microcrystalline cellulose. Additional excipients, including one or more diluents or fillers can also be included, as recognized and determined by a person of ordinary skill in the art. For example, a preferred embodiment of the subject invention includes microcrystalline cellulose, magnesium stearate (also considered to have lubricant properties), and colloidal silicon dioxide as fillers or diluents.

In order to provide an initial release of a portion of the active drug from the dosage form in an acidic pH environment, and therefore allow bioavailability of the active drug while the dissolving dosage form may still be present in the stomach or other enteric areas having a pH lower than 5.5, an immediate release (IR) coating containing a portion of the total dose within the IR coat can be provided as part of the dosage form. For example, a preferred embodiment of the subject invention comprises an IR coating comprising methylphenidate, or an analog, derivative, isomer or prodrug of methylphenidate, a solubilizer, such as a hydrogel, e.g., hypromellose (hydroxypropyl methylcellulose, or HPMC), a surfactant, such as polyethylene glycol, and a filler, e.g., talc. Color coatings, such as those marketed under the brand name, Opadry®, which are known in the pharmaceutical arts, can also be used as desired.

Preferably, a seal coat is provided between the compressed tablet core and the IR active layer. The seal coat is preferably an inert or inactive composition, i.e., containing no active drug, and can comprise a polymeric compound, such as a cellulosic hydrogel, e.g., HPMC, as a film-former, a surfactant, such as polyethylene glycol, and a filler, such as talc. The composition of the seal coat can also comprise a pigment, such as titanium dioxide. The final dosage form can also include a seal coat surrounding the IR layer.

A preferred manufacturing process and a resulting dosage form according to the subject invention is described in detail below in the context of the label claim for a tablet containing 54 mg methylphenidate HCl. Other strengths of the product are prepared using proportionate amounts of active ingredient and proportionate amounts of excipients. All of the ingredient weights provided below are provided as weight:weight unless otherwise noted. The amounts of active ingredient and excipients are understood as target amounts and may contain slight variations from those specified target amounts. It is fully expected that variations from these target amount values may occur due to process variability and are considered to be within the scope of the subject invention. For example, the exact amount of coated beads added to the final blend may vary in view of the in-process assay results determined for the beads as would be understood in the art.

EXAMPLE 1

Bioequivalent Formulation A

Manufacturing steps for preparing a dosage form of the subject invention are as follows:
(1) Active Coated Beads
To obtain Active Beads weighing 137.07 mg, sugar spheres (35.55 mg) are coated with a mixture of 42.66 mg methylphenidate HCl, 4.28 mg hypromellose, and 4.28 mg talc prepared in purified water and using 0.1 N HCl q.s. the desired pH of about 3.0. The water is evaporated away and, as in all steps of this process, is negligible in the final product.

(2) Sustained Release Bead Coating (Bead Coating 1)
The Active Beads are then coated with a Sustained Release Coating solution consisting of ethylcellulose (16.91 mg), hydroxypropyl cellulose (2.54 mg), triethyl citrate (3.38 mg) and talc (5.07 mg) in a 75:25 mixture of isopropyl alcohol and purified water, yielding Sustained Release Coated Beads weighing 164.97 mg. The isopropyl alcohol and water are evaporated to a negligible amount in the final product.

(3) Controlled Release Bead Coating (Bead Coatng 2)
The Sustained Release Coated Beads are then further coated with a Controlled Release Coating solution consisting of 22.40 mg hypromellose acetate succinate in an 80:20 mixture of ethanol (96%) and purified water. The Controlled Release Coated Beads for one tablet weigh 187.37 mg. The ethanol and water are evaporated away to negligible amounts in the final product.

(4) Final Blend And Tablet Core
The Controlled Release Coated Beads are then blended with 112.92 mg carboxymethylcellulose sodium, 118.99 mg microcrystalline cellulose, 2.79 mg magnesium stearate, 2.79 mg colloidal silicon dioxide, and 1.86 mg black iron oxide to form the Final Blend. The Final Blend is then compressed to form the tablet cores, each weighing about 426.72 mg. A Seal Coating Solution is prepared comprising 3.30 mg titanium dioxide, 11.10 mg hypromellose, 3.15 mg polyethylene glycol 4000 and 1.65 mg talc, in purified water. About 40% of the Seal Coating Solution is used to coat the Tablet Cores.

(5) Active Immediate-Release Coat And Final Tablet
An Active Immediate-Release Coating solution consisting of 11.34 mg methylphenidate HCl, 5.67 mg hypromellose, 2.94 mg polyethylene glycol 4000, and 3.57 mg talc, in purified water and using 0.1 N HCl q.s. the desired pH of about 3.0 is prepared and applied onto the seal-coated tablet cores. The remaining 60% portion of the Seal Coating Solution is then applied over the Active Immediate-release Coating. A Color Coating solution of 13.23 mg colorant (Pink Opadry®) in purified water is applied to the tablet and a negligible amount of Black Opacode® is used to print the tablet with the identifier. The final tablet weight is approximately 432.37 mg.

The above formulation for a tablet of the subject invention is presented in table form (Table 1), below:

TABLE 1

| Formulation A | | |
|---|---|---|
| Component | Percent of Tablet (%) | Amount per Tablet (mg/tablet) 54 mg |
| ACTIVE COAT | | |
| Methylphenidate HCl USP | 9.87 | 42.66 |
| Sugar Spheres NF 45-60 Mesh | 8.22 | 35.55 |
| Hypromellose 2910 USP (Methocel E-5 Premium) | 0.99 | 4.28 |
| Talc USP | 0.99 | 4.28 |
| Hydrochloric Acid 1.0N[4] | 0.00 | |
| BEAD COATING 1 | | |
| Ethylcellulose NF (Ethocel 45) | 3.91 | 16.91 |
| Hydroxypropyl Cellulose NF (Klucel EF) | 0.59 | 2.54 |
| Triethyl Citrate NF | 0.78 | 3.38 |
| Talc USP | 1.17 | 5.07 |
| Isopropyl Alcohol USP[2] | 0.00 | |

TABLE 1-continued

Formulation A

| Component | Percent of Tablet (%) | Amount per Tablet (mg/tablet) 54 mg |
|---|---|---|
| BEAD COATING 2[1] | | |
| Hypromellose Acetate Succinate NF (AQOAT-LG) | 5.18 | 22.40 |
| Alcohol (Ethanol) USP[3] | 0.00 | |
| SUB-TOTAL | | 137.07 |
| Methylphenidate HCl Common Bead Intermediate | | |
| FINAL BLEND | | |
| Carboxymethylcellulose Sodium USP | 26.12 | 112.92 |
| Microcrystalline Cellulose NF (Avicel PH101) | 27.52 | 118.99 |
| Magnesium Stearate NF Powder (non-Bovine) | 0.65 | 2.79 |
| Colloidal Silicon Dioxide NF (Aerosil 200) | 0.65 | 2.79 |
| Mapico Black EC 848 | 0.43 | 1.86 |
| ACTIVE IR COATING[1] | | |
| Methylphenidate HCl USP | 2.62 | 11.34 |
| Hypromellose 2910 USP (Methocel E-5 Premium) | 1.31 | 5.67 |
| Polyethylene Glycol 4000 NF | 0.68 | 2.94 |
| Talc USP | 0.83 | 3.57 |
| Hydrochloric Acid 1.0N[4] | 0.00 | |
| SEAL COATING[1] | | |
| Titanium Dioxide USP | 0.76 | 3.30 |
| Hypromellose 2910 USP (Methocel E-5 Premium) | 2.57 | 11.10 |
| Polyethylene Glycol 4000 NF | 0.73 | 3.15 |
| Talc USP | 0.38 | 1.65 |
| COLOR COATING[1] | | |
| Pink Opadry YS-5-14728 | 3.06 | 13.23 |
| TABLET PRINTING | | |
| Black Opacode WB NS-78-17821 | 0.00 | Negligible |
| TOTAL | 100 | 432.37 |

[1]Purified Water is used in the coating solution but is evaporated during processing.
[2]Isopropyl Alcohol is used in the coating solution but is evaporated during processing.
[3]Alcohol (Ethanol) is used in the coating solution but is evaporated during processing.
[4]Hydrochloric Acid 1.0N is used to adjust the pH.

For tablets containing 18, 27, and 36 mg of methylphenidate, the above formulation is followed, using proportionate amounts of active ingredient and inactive ingredients.

EXAMPLE 2

Bioequivalent Formulation B

Manufacturing steps for preparing an alternative embodiment of a dosage form of the subject invention are as follows:

(1) Active Beads

To obtain Active Beads weighing 93.35 mg, sugar spheres (38.25 mg) are coated with a mixture of 45.90 mg methylphenidate HCl, 4.6 mg hypromellose, and 4.6 mg talc prepared in purified water and using 0.1 N HCl q.s. the desired pH of about 3.0. The water is evaporated away and, as in all steps of this process, is negligible in the final product.

(2) Sustained Release Bead Coating

The Active Beads are then coated with a Sustained Release Coating solution consisting of ethylcellulose (18.20 mg), hydroxypropyl cellulose (2.73 mg), triethyl citrate (3.63 mg) and talc (5.46 mg) in a 75:25 mixture of isopropyl alcohol and purified water, yielding Sustained Release Coated Beads weighing 123.37 mg. The isopropyl alcohol and water are evaporated to a negligible amount in the final product.

(3) Controlled Release Bead Coating

The Sustained Release Coated Beads are then further coated with a Controlled Release Coating solution consisting of 24.10 mg hypromellose acetate succinate in an 80:20 mixture of ethanol (96%) and purified water. The Controlled Release Coated Beads for one tablet weigh 147.47 mg. The ethanol and water are evaporated away to negligible amounts in the final product.

(4) Final Blend And Tablet Core

The Controlled Release Coated Beads are then blended with 121.50 mg carboxymethylcellulose sodium, 128.03 mg microcrystalline cellulose, 3.0 mg magnesium stearate, 3.0 mg colloidal silicon dioxide, and 2.0 mg black iron oxide to form the Final Blend. The Final Blend is then compressed to form the tablet cores, each weighing about 405.00 mg. A Seal Coating Solution is prepared comprising 3.30 mg titanium dioxide, 11.10 mg hypromellose, 3.15 mg polyethylene glycol 4000 and 1.65 mg talc, in purified water. About 40% of the Seal Coating Solution is used to coat the Tablet Cores.

(5) Active Immediate-Release Coat And Final Tablet

An Active Immediate-Release Coating solution consisting of 8.10 mg methylphenidate HCl, 4.05 mg hypromellose, 2.10 mg polyethylene glycol 4000, and 2.55 mg talc, in purified water and using 0.1 N HCl q.s. the desired pH of about 3.0 is prepared and applied onto the seal-coated tablet cores. The remaining 60% portion of the Seal Coating Solution is then applied over the Active Immediate-release Coating. A Color Coating solution of 13.23 mg colorant (Pink Opadry®) in purified water is applied to the tablet and a negligible amount of Black Opacode® is used to print the tablet with the identifier. The final tablet weight is approximately 454.23 mg.

EXAMPLE 3

Dissolution

Dissolution testing was conducted using 18, 27, 36, and 54 mg Methylphenidate HCl Extended Release Tablets of the subject invention, manufactured in accordance with Formulation B. The dissolution medium was pH 6.8 Phosphate Buffer in Apparatus USP Type I (baskets) at 100 rpm, in 900 mL of dissolution media. The results of the dissolution testing are reproduced below in Table 2:

TABLE 2

Dissolution results

| | | % Released | | | | | | | | | | | |
|---|---|---|---|---|---|---|---|---|---|---|---|---|---|
| Strength | Lot | Hr 1 | Hr 2 | Hr 3 | Hr 4 | Hr 5 | Hr 6 | Hr 7 | Hr 8 | Hr 9 | Hr 10 | Hr 11 | Hr 12 |
| 18 mg | P90170 | 15 | 24 | 40 | 54 | 65 | 74 | 80 | 84 | 88 | 90 | 91 | 92 |
| 27 mg | P80160 | 14 | 23 | 36 | 48 | 58 | 66 | 72 | 76 | 79 | 81 | 83 | 84 |

TABLE 2-continued

Dissolution results

% Released

| Strength | Lot | Hr 1 | Hr 2 | Hr 3 | Hr 4 | Hr 5 | Hr 6 | Hr 7 | Hr 8 | Hr 9 | Hr 10 | Hr 11 | Hr 12 |
|---|---|---|---|---|---|---|---|---|---|---|---|---|---|
| 36 mg | P80150 | 13 | 21 | 33 | 47 | 59 | 68 | 74 | 78 | 85 | 88 | 94 | 94 |
| 54 mg | P80280 | 15 | 22 | 34 | 48 | 60 | 70 | 77 | 82 | 86 | 89 | 91 | 92 |

All hourly results are based on an average from n = 12 vessels

EXAMPLE 4

Bioequivalence

Bioequivalency studies were also conducted using the dosage forms of the subject formulation, manufactured in accordance with Formulation B, and selected results are shown below in Tables 3-5.

TABLE 3

Summary of Results - Methylphenidate in Plasma

Pharmacokinetic Parameters

|  | ln AUC 0-t* (ng · h/mL) | ln AUCinf* (ng · h/mL) | ln Cmax* (ng/mL) | tmax (h) | Half-life (h) | kel (1/h) |
|---|---|---|---|---|---|---|
| Mean | 133.247 | 137.034 | 12.79905 | 6.321 | 5.019 | 0.1402 |
| CV | 31.8 | 32.2 | 32.8 | 15.6 | 12.5 | 12.6 |
| n | 28 | 28 | 28 | 28 | 28 | 28 |

Least-Squares Means
Kremers Urban (A) 133.247 137.034 12.79905
Ratio of Least-Squares Means
(A/B) % 97.0 98.7 100.0
90% Confidence Intervals
(A/B) %
lower limit: 92.8% 94.5% 94.4%
upper limit: 101.4% 103.1% 106.0%
p-Value (ANOVA)
A vs B 0.2489 0.6165 0.9929
Period 0.2650 0.2344 0.2593
Sequence 0.1980 0.1937 0.2040
Intrasubject CV % 9.7 9.6 12.9
*For ln-transformed parameters, the antilog of the mean (i.e. the geometric mean) is reported.

TABLE 4

Concentration Tables - Methylphenidate in Plasma

Concentrations (ng/mL) at Each Sampling Time (h)
Time (hrs)

| Subj. ID | 0 | 0.5 | 1 | 2 | 3 | 4 | 5 | 6 | 7 | 8 | 9 | 10 | 12 | 16 | 20 | 24 | 30 |
|---|---|---|---|---|---|---|---|---|---|---|---|---|---|---|---|---|---|
| 1 | BLQ | BLQ | 0.757 | 3.87 | 6.38 | 7.99 | 15.40 | 24.30 | 21.90 | 22.80 | 18.20 | 15.60 | 12.50 | 11.40 | 6.86 | 5.11 | 2.14 |
| 2 | BLQ | 2.40 | 6.44 | 7.63 | 9.09 | 12.20 | 19.20 | 20.40 | 18.50 | 16.80 | 13.30 | 10.80 | 8.28 | 5.05 | 3.16 | 1.97 | 0.478 |
| 3 | BLQ | 0.268 | 2.15 | 4.35 | 4.11 | 3.93 | 5.80 | 10.30 | 10.10 | 9.99 | 8.92 | 7.32 | 5.88 | 3.34 | 2.13 | 1.32 | 0.598 |
| 4 | BLQ | 0.197 | 1.32 | 3.68 | 3.93 | 3.67 | 5.82 | 10.90 | 11.20 | 11.60 | 10.00 | 9.16 | 8.88 | 5.66 | 3.36 | 2.00 | 0.866 |
| 5 | BLQ | 0.691 | 4.30 | 4.50 | 5.43 | 6.30 | 12.00 | 16.10 | 12.70 | 12.00 | 8.86 | 8.02 | 5.74 | 2.99 | 1.43 | 0.84 | 0.288 |
| 6 | BLQ | 4.44 | 7.51 | 5.83 | 7.80 | 8.10 | 12.40 | 11.00 | 9.29 | 8.42 | 7.18 | 6.42 | 5.12 | 2.52 | 1.33 | 1.01 | 0.272 |
| 7 | BLQ | 2.12 | 6.24 | 6.22 | 9.16 | 9.10 | 13.30 | 19.40 | 18.80 | 16.10 | 13.00 | 13.00 | 10.60 | 5.84 | 3.09 | 1.96 | 0.624 |
| 8 | BLQ | 0.127 | 1.76 | 3.26 | 3.88 | 5.02 | 6.74 | 8.32 | 8.66 | 7.23/T | 7.16 | 6.92 | 5.45 | 3.51 | 1.86 | 1.14 | 0.413 |
| 9 | BLQ | 0.964 | 5.41 | 10.50 | 11.80 | 12.90/T | 23.20 | 25.90 | 20.00 | 15.10/T | 12.40 | 9.08 | 6.36 | 3.77 | 2.23 | 1.20 | 0.456 |
| 10 | BLQ | 0.514 | 2.10 | 3.66 | 3.92 | 4.68 | 9.29 | 12.30 | 12.20 | 11.60 | 9.41 | 8.60 | 6.71 | 4.14 | 2.53 | 1.38 | 0.547 |
| 11 | BLQ | 0.884 | 5.88 | 7.55 | 7.28 | 7.97 | 18.40 | 18.00 | 16.60 | 14.80 | 12.00 | 9.77 | 5.93 | 3.00 | 1.77 | 0.931 | 0.365 |
| 12 | BLQ | 0.698/T | 2.18 | 3.03 | 4.88 | 5.80 | 8.29 | 8.58 | 10.30 | 9.10 | 8.75 | 7.16 | 5.99 | 3.20 | 1.98 | 1.35 | 0.492 |
| 13 | BLQ | 0.592 | 1.99 | 3.08 | 3.06 | 3.32 | 6.18 | 8.16 | 9.31 | 8.67 | 6.81 | 6.11 | 5.29 | 2.98 | 1.46 | 0.848 | 0.284 |
| 14 | BLQ | 0.203 | 1.30 | 3.23 | 3.27 | 3.88 | 8.31 | 9.04 | 9.31 | 8.72 | 7.17 | 6.43 | 5.20 | 3.24 | 2.12 | 1.53 | 0.580 |
| 15 | BLQ | 1.05/T | 2.30 | 3.08 | 3.73 | 4.49 | 7.12 | 8.82 | 8.52 | 8.61 | 7.82 | 7.17 | 4.77 | 3.06 | 1.69 | 0.988 | 0.369 |
| 16 | BLQ | 1.24 | 3.91 | 3.51 | 4.98 | 8.35 | 11.20 | 9.97 | 9.89 | 10.70 | 8.73 | 6.89 | 5.28 | 3.16 | 2.22 | 1.53 | 0.566 |

TABLE 4-continued

Concentration Tables - Methylphenidate in Plasma

Concentrations (ng/mL) at Each Sampling Time (h)
Time (hrs)

| Subj. ID | 0 | 0.5 | 1 | 2 | 3 | 4 | 5 | 6 | 7 | 8 | 9 | 10 | 12 | 16 | 20 | 24 | 30 |
|---|---|---|---|---|---|---|---|---|---|---|---|---|---|---|---|---|---|
| 17 | BLQ | 0.132 | 2.94/T | 4.94 | 5.26 | 5.82 | 14.70 | 17.40 | 14.50 | 10.60 | 9.65 | 6.65 | 4.54 | 2.95 | 1.95 | 1.43 | 0.520 |
| 18 | BLQ | 1.05 | 2.92 | 4.05 | 4.99 | 5.72 | 11.40 | 11.80 | 13.20 | 11.70 | 8.95 | 8.68 | 6.48 | 3.69 | 2.47 | 1.53 | 0.518 |
| 19 | BLQ | 0.53 | 1.79 | 3.03 | 3.07 | 4.23 | 11.00 | 13.00 | 11.60 | 11.80 | 9.06 | 7.84 | 5.87 | 3.15 | 1.91 | 1.32 | 0.395 |
| 20 | BLQ | 0.43 | 2.81 | 3.55 | 4.53 | 6.05 | 9.24 | 10.20 | 12.30 | 10.80 | 11.40 | 7.79 | 6.16 | 3.62 | 2.24 | 1.35 | 0.438 |
| 21 | BLQ | 0.391 | 2.50 | 2.75 | 3.91 | 4.47 | 7.62 | 8.01 | 7.75 | 7.56 | 8.71 | 6.86 | 5.54 | 2.91 | 1.95 | 0.86 | 0.311 |
| 22 | BLQ | 0.271 | 1.99 | 2.90 | 3.44 | 3.44 | 7.23 | 9.96 | 8.36 | 8.37 | 6.32 | 5.40 | 4.55 | 2.79 | 1.83 | 1.11 | 0.438 |
| 23 | BLQ | 0.664 | 2.59 | 4.22 | 5.23 | 6.67 | 13.30 | 13.90 | 13.80 | 14.70 | 13.20 | 11.70 | 8.71 | 5.39 | 3.59 | 2.28 | 0.917 |
| 24 | BLQ | 1.120 | 3.91 | 4.38 | 4.79 | 5.94 | 8.92 | 10.70 | 8.71 | 9.08 | 6.82 | 6.52 | 4.91 | 2.91 | 2.02 | 1.12 | 0.474 |
| 25 | BLQ | 0.508 | 2.87 | 3.71 | 4.80 | 6.94 | 16.40 | 16.00 | 15.20 | 14.20 | 11.10 | 9.10 | 5.89 | 4.08 | 2.56 | 1.79 | 0.656 |
| 26 | BLQ | 0.139 | 1.43 | 2.69 | 3.09 | 3.95 | 8.07 | 7.79 | 6.91 | 5.67 | 4.63 | 4.46 | 3.29 | 1.47 | 0.862 | 0.51 | 0.155 |
| 27 | BLQ | 0.509 | 2.74 | 4.06 | 4.49 | 5.24 | 10.40 | 10.90 | 8.10 | 5.89 | 4.33 | 3.45 | 2.13 | 0.919 | 0.47 | 0.252 | BLQ |
| 28 | BLQ | 1.380 | 5.09 | 4.73 | 5.19 | 6.44 | 11.80 | 13.30 | 13.50 | 12.40 | 10.40 | 10.10 | 8.85 | 5.19 | 3.65 | 2.30 | 1.030 |

BLQ—Below Limit of Quantitation
BLQ values are set to zero for statistics.

TABLE 5

Pharmacokinetic Parameter Tables - Methylphenidate in Plasma

| Subject ID | AUC 0-t (ng·h/mL) | AUCinf (ng·h/mL) | AUC/AUCinf (%) | Cmax (ng/mL) | tmax (h) | t½ (h) | kel (1/h) | kelStart (h) | kel top (h) |
|---|---|---|---|---|---|---|---|---|---|
| 1 | 287.3 | 305.7 | 94.0 | 24.300 | 6.00 | 5.94 | 0.117 | 16.00 | 30.00 |
| 2 | 208.3 | 211.4 | 98.5 | 20.400 | 6.00 | 4.51 | 0.154 | 12.00 | 30.00 |
| 3 | 118.1 | 122.9 | 96.1 | 10.300 | 6.00 | 5.54 | 0.125 | 12.00 | 30.00 |
| 4 | 150.9 | 157.6 | 95.8 | 11.600 | 8.00 | 5.34 | 0.130 | 12.00 | 30.00 |
| 5 | 133.5 | 135.2 | 98.7 | 16.100 | 6.00 | 4.20 | 0.165 | 12.00 | 30.00 |
| 6 | 124.1 | 125.9 | 98.6 | 12.400 | 5.00 | 4.46 | 0.156 | 12.00 | 30.00 |
| 7 | 209.5 | 213.6 | 98.1 | 19.400 | 6.00 | 4.49 | 0.154 | 12.00 | 30.00 |
| 8 | 106.8 | 109.7 | 97.4 | 8.660 | 7.00 | 4.83 | 0.144 | 12.00 | 30.00 |
| 9 | 200.3 | 203.4 | 98.5 | 25.900 | 6.00 | 4.73 | 0.146 | 12.00 | 30.00 |
| 10 | 137.1 | 140.9 | 97.3 | 12.300 | 6.00 | 4.76 | 0.146 | 16.00 | 30.00 |
| 11 | 164.7 | 167.1 | 98.6 | 18.400 | 5.00 | 4.52 | 0.153 | 12.00 | 30.00 |
| 12 | 118.3 | 122.0 | 97.0 | 10.300 | 7.00 | 5.17 | 0.134 | 12.00 | 30.00 |
| 13 | 98.3 | 100.0 | 98.3 | 9.310 | 7.00 | 4.18 | 0.166 | 16.00 | 30.00 |
| 14 | 110.1 | 115.0 | 95.7 | 9.310 | 7.00 | 5.88 | 0.118 | 12.00 | 30.00 |
| 15 | 104.4 | 107.0 | 97.6 | 8.820 | 6.00 | 4.85 | 0.143 | 12.00 | 30.00 |
| 16 | 127.9 | 132.7 | 96.4 | 11.200 | 5.00 | 5.81 | 0.119 | 12.00 | 30.00 |
| 17 | 136.8 | 141.3 | 96.8 | 17.400 | 6.00 | 5.95 | 0.116 | 12.00 | 30.00 |
| 18 | 140.8 | 144.6 | 97.4 | 13.200 | 7.00 | 5.09 | 0.136 | 12.00 | 30.00 |
| 19 | 125.8 | 128.5 | 97.9 | 13.000 | 6.00 | 4.82 | 0.144 | 12.00 | 30.00 |
| 20 | 132.1 | 135.1 | 97.7 | 12.300 | 7.00 | 4.82 | 0.144 | 12.00 | 30.00 |
| 21 | 104.4 | 106.4 | 98.2 | 8.710 | 9.00 | 4.35 | 0.159 | 12.00 | 30.00 |
| 22 | 98.7 | 102.2 | 96.7 | 9.960 | 6.00 | 5.40 | 0.128 | 12.00 | 30.00 |
| 23 | 181.0 | 188.5 | 96.0 | 14.700 | 8.00 | 5.64 | 0.123 | 12.00 | 30.00 |
| 24 | 114.1 | 117.8 | 96.9 | 10.700 | 6.00 | 5.39 | 0.129 | 12.00 | 30.00 |
| 25 | 159.6 | 165.0 | 96.7 | 16.400 | 5.00 | 5.78 | 0.120 | 12.00 | 30.00 |
| 26 | 72.9 | 73.8 | 98.7 | 8.070 | 5.00 | 4.23 | 0.164 | 12.00 | 30.00 |
| 27 | 73.3 | 74.8 | 98.1 | 10.900 | 6.00 | 3.92 | 0.177 | 12.00 | 24.00 |
| 28 | 173.9 | 182.7 | 95.2 | 13.500 | 7.00 | 5.94 | 0.117 | 12.00 | 30.00 |

Thus, the subject invention provides a dosage form which can release the active drug in a manner which is bioequivalent to Concerta®, without requiring the use of expensive multi-layered tabletting machines, and without providing complex ascending release profiles. The dosage form according to the subject invention is a non-push-layer formulation, comprising a single-layer tablet core formed by compression of coated beads or pellets, and comprising an immediate release coating comprising active drug present on the coated-bead compressed core.

The foregoing is exemplary and illustrative of compositions and products concerning the present invention, but it is to be understood that they are not limiting and may also relate to dosage forms for application of sustained release ingredients such as vaginal and rectal suppositories. The tablets of the subject invention particularly act on oral, oropharyngeal, gastric, and intestinal regions of the gut. The total dosage is governed by usual medical considerations or physician's directions and when sufficiently large doses of active medicament are incorporated in the unit dosage form, systemic as well as local action is obtained to overcome or control the pathological condition or disorder being treated.

The invention claimed is:

1. A pharmaceutical dosage form exhibiting both immediate release and extend release properties comprising a therapeutically effective amount of active drug selected from methylphenidate and d-threo-methylphenidate comprising:
  a) a tablet core comprising a compressed mixture of coated sugar spheres and a blend of carboxymethylcellulose, microcrystalline cellulose, magnesium stearate, silicon dioxide, and black iron oxide, said coated sugar spheres comprising
  i. an active drug layer comprising the active drug, hypromellose and talc;
  ii. a sustained release coating comprising ethylcellulose, hydroxypropyl cellulose, triethyl citrate, and talc; and
  iii. a controlled release enteric coating comprising hvpromellose acetate succinate; and
b) an immediate release drug coat on said tablet core, said immediate release drug coat comprising active drug, hypromellose, polyethylene glycol, and talc.

2. The dosage form of claim 1 wherein said tablet further comprises a seal coating comprising titanium dioxide, hypromellose, polyethylene glycol and talc between the tablet core and the active immediate release coat.

3. The dosage form of claim 2 wherein the dosage form further comprises a second seal coat comprising titanium dioxide, hypromellose, polyethylene glycol and talc overlying the immediate release drug coat and optionally a color coat over said second seal coat.

4. The dosage form of claim 1 wherein wherein the composition of the dosage form is the dosage form is a tablet and wherein the tablet core comprises:

| | |
|---|---|
| Carboxymethylcellulose Sodium | 26.12 wt % |
| Microcrystalline Cellulose | 27.52 wt % |
| Magnesium Stearate | 0.65 wt % |
| Colloidal Silicon Dioxide | 0.65 wt % |
| Iron Oxide | 0.43 wt % | wherein the active drug layer comprises:

| | |
|---|---|
| Methylphenidate or d-threo-methylphenidate | 9.87 wt % |
| Sugar Spheres | 8.22 wt % |
| Hypromellose | 0.99 wt % |
| Talc | 0.99 wt % | wherein the sustained release coating comprises:

| | |
|---|---|
| Ethylcellulose | 3.91 wt % |
| Hydroxypropyl Cellulose | 0.59 wt % |
| Triethyl Citrate | 0.78 wt % |
| Talc | 1.17 wt % | wherein the controlled release enteric coating comprises:

| | |
|---|---|
| Hypromellose Acetate Succinate | 5.18 wt % | and wherein the immediate release drug coating comprises:

| | |
|---|---|
| Methylphenidate HCl or d-threo-methylphenidate | 2.62 wt % |
| Hypromellose | 1.31 wt % |
| Polyethylene Glycol | 0.68 wt % |
| Talc | 0.83 wt %. |

5. The dosage form of claim 4, further comprising a seal coat underlying the immediate release drug coating, said seal coat comprising titanium dioxide, hypromellose, polyethylene glycol and talc.

6. The dosage form of claim 4, further comprising a seal coat overlying the immediate release drug coating, said seal coat comprising titanium dioxide, hypromellose, polyethylene glycol and talc.

7. The dosage form of claim 4 further comprising an outer color coating.

8. The dosage form of claim 1, wherein the dosage form is a tablet, and wherein the tablet core comprises:

| | |
|---|---|
| Carboxymethylcellulose Sodium | 121.50 mg |
| Microcrystalline Cellulose | 128.03 mg |
| Magnesium Stearate | 3.0 mg |
| Colloidal Silicon Dioxide | 3.0 mg |
| Iron Oxide | 2.0 mg | wherein the active drug layer comprises:

| | |
|---|---|
| Methylphenidate or d-threo-methylphenidate | 45.90 mg |
| Sugar Spheres | 38.25 mg |
| Hypromellose | 4.6 mg |
| Talc | 4.6 mg | wherein the sustained release coating comprises:

| | |
|---|---|
| Ethylcellulose | 18.20 mg |
| Hydroxypropyl Cellulose | 2.73 mg |
| Triethyl Citrate | 3.63 mg |
| Talc | 5.46 mg | wherein the controlled release enteric coating comprises:

| | |
|---|---|
| Hypromellose Acetate Succinate | 24.10 mg | wherein the immediate release drug coating comprises:

| | |
|---|---|
| Methylphenidate HCl or d-threo-methylphenidate | 8.10 mg |
| Hypromellose | 4.05 mg |
| Polyethylene Glycol | 2.10 mg |
| Talc | 2.55 mg |
| Color coating | 13.23 mg | or a tablet having proportionate amounts of the above recited ingredients relative to an amount of methylphenidate or de-threo-methylphenidate of 18-54 mg.

9. The dosage form of claim 8, further comprising a seal coat underlying the immediate release drug coating, said seal coat comprising titanium dioxide, hypromellose, polyethylene glycol and talc.

10. The dosage form of claim 8, further comprising a seal coat overlying the immediate release drug coating said seal coat comprising titanium dioxide, hypromellose, polyethylene glycol and talc.

11. The dosage form of claim 8 further comprising an outer color coating.

12. A method of manufacturing a dosage form of claim 1 for the treatment of Attention Deficit Disorder or Attention Deficit/Hyperactivity Disorder in a patient in need thereof, said method comprising:
  forming an active bead or pellet comprising an active drug selected from methylphenidate and d-threo-methylphenidate, coating the active bead or pellet with a sustained-release coating and a controlled release coating to form coated active beads or pellets, forming a tablet core using said coated active beads or pellets, and coating said tablet core with an immediate-release coating comprising the active drug.

13. The method of claim 12 wherein said method further comprises providing a seal coat between the tablet core and the immediate release coat.

14. A method for treating Attention Deficit Disorder or Attention Deficit/Hyperactivity Disorder in a patient in need thereof, said method comprising:

providing a dosage form of claim 1, and administering said dosage form to the patient.

* * * * *